United States Patent [19]

Datta

[11] Patent Number: 5,021,595

[45] Date of Patent: Jun. 4, 1991

[54] TRANSITION METAL CATALYST COMPOSITION FOR OLEFIN POLYMERIZATION

[75] Inventor: Sudhin Datta, Matawan, N.J.

[73] Assignee: Exxon Chemical Patents Inc., Linden, N.J.

[21] Appl. No.: 487,695

[22] Filed: Mar. 2, 1990

[51] Int. Cl.$^5$ .......................... C07C 9/00; C07C 7/00; C07C 11/00

[52] U.S. Cl. .......................................... 556/42; 556/1; 556/51; 502/102; 502/150; 502/103; 502/117

[58] Field of Search .................. 556/1, 42, 51, 4, 150; 502/112, 117, 102, 103

[56] References Cited

U.S. PATENT DOCUMENTS

| | | | |
|---|---|---|---|
| 4,066,571 | 1/1978 | Columberg | 252/431 |
| 4,069,055 | 1/1978 | Crivello | 556/42 X |
| 4,351,775 | 9/1982 | Magee, Jr. | 556/42 |
| 4,373,079 | 2/1983 | Parziale et al. | 556/42 X |
| 4,508,842 | 2/1985 | Beran et al. | 502/112 |
| 4,540,753 | 9/1985 | Cozewith et al. | 526/88 |
| 4,758,682 | 7/1988 | Collins et al. | 556/42 X |

Primary Examiner—Arthur C. Prescott
Attorney, Agent, or Firm—M. L. Gibbons

[57] ABSTRACT

This invention relates to bidentate transition metal catalyst compositions useful for coordination polymerization of alpha olefin monomers. The novel catalyst compounds are prepared by:

(1) reacting a transition trihalide, a transition metal trialkoxide or mixed tri(halide/alkoxide), or the adducts of these materials with Lewis bases, with two equivalents of a bidentate chelating ligand; or (2) reacting two equivalents of the same or different transition metal (+3) tris chelates with one equivalent of a transition metal trihalide or its adduct with Lewis bases.

The invention chelating ligands are those which contain at least two, and preferably not more than two, hetero atoms such as O, N, P, or S, separated by a hydrocarbon radical providing sufficient chain length so as to allow both hetero atoms to chelate the same metal atom. The chelating ligand must have at least one easily removable positive ion which is lost on chelation to afford a uninegative, bidentate ligand.

67 Claims, No Drawings

TRANSITION METAL CATALYST COMPOSITION FOR OLEFIN POLYMERIZATION

BACKGROUND OF THE INVENTION

1. Field of the Invention

The present invention pertains to novel coordination polymerization catalysts having utility for the polymerization and copolymerization of ethylene and alpha olefins and optionally diene monomers. More specifically the invention relates to hydrocarbon soluble Ziegler catalysts that contain bidentate ligands on transition metal compounds such as those based on vanadium.

2. Description of Related Art

Ethylene-alpha-olefin copolymers, particularly elastomers, are important commercial products. Of these, copolymers of ethylene and propylene are especially important. Two basic types of ethylene-propylene copolymers are commercially available. Ethylene-propylene copolymers (EPM) are saturated compounds requiring vulcanization with free radical generators such as organic peroxides. Ethylene-alpha-olefin terpolymers (e.g., EPDM) contain a small amount of non-conjugated diolefin, such as dicyclopentadiene, 1,4-hexadiene or 5-ethylidene-2-norbornene (ENB), which provides sufficient unsaturation to permit vulcanization with curing agents other than peroxides, such as sulfur. Such polymers that include at least two monomers, e.g., EPM and EPDM, will hereinafter be collectively referred to as ethylene-based copolymers.

These copolymers have outstanding resistance to weathering, good heat aging properties and the ability to be compounded with large quantities of fillers and plasticizers resulting in low cost compounds which are particularly useful in automotive and industrial mechanical goods applications. Typical automotive uses are tire sidewalls, inner tubes, radiator and heater hose, vacuum tubing, weather stripping and sponge doorseals and Viscosity Index improvers for lubricating oil compositions. Typical mechanical goods uses are for appliance, industrial and garden hoses, both molded and extruded sponge parts, gaskets and seals and conveyor belt covers. These copolymers also find use in adhesives, appliance parts as in hoses and gaskets, wires and cable and plastics blending.

The properties of these ethylene-based copolymers are a function of the catalyst system and polymerization process used to produce them. Elastomeric olefin copolymers may be produced at relatively low polymerization temperatures and pressures by means of the so called Ziegler - Natta catalysts which comprise a transition metal compound used in combination with a metal alkyl. More specifically, certain catalyst systems based on a combination of a vanadium compound, an aluminum alkyl or aluminum alkyl halide and, in some cases, a halogen-containing organic compound which serves as a polymerization promoter are known in the art.

For example, U.S. Pat. No. 4,540,753 relates to ethylene copolymers with narrow molecular weight distribution (MWD) and a narrow inter molecular compositional distribution (CD). The catalyst system used in this reference may comprise $VCl_4$, or pentavalent or trivalent hydrocarbon-soluble vanadium compound having the formula:

$$VCl_x(OR)_{3-x}$$

where x is 0-3 and R is a hydrocarbon radical, and an organo-aluminum compound. In the polymerization process, the catalyst components are premixed in the premixing device and aged for 1-50 seconds.

U.S. Pat. No. 4,508,842 discloses gas phase homo or copolymerization of ethylene using a supported catalysts made by treating $VCl_3$ with a Lewis base. The Lewis bases taught in the patent are not chelating agents, but rather monodentate ligands.

U.S. Pat. No. 4,066,571 discloses that polymerization catalysts can be made by treating transition metal salts with acetylating agents. In example 7 therein, the salt acetylated is $VCl_3$. Vanadium compounds are also used in Examples 15 and 33 thereof.

Though not directed to coordination polymerization or to catalyst compounds useful therein, Cotton et al. Inorg. Chem. 25 3505-3512 (1986) discloses certain vanadium carboxylates and utilizes acetic acid in preparing the same. No utility is taught for the resulting product. Additionally, since the Cotton et al, product will be largely insoluble in hydrocarbon solvents, it would not appear to have utility in Ziegler solution polymerization where hydrocarbon soluble catalysts are required.

In the area of ethylene and alpha olefin polymerization, a need has existed for the development of new hydrocarbon soluble Ziegler polymerization systems which have the capability of polymerizing at higher temperatures in continuous flow stirred tank reactor (CFSTR) polymerization reactions than those used with traditional catalyst such as $VCl_4$, without having the catalyst efficiency decrease as significantly as at temperatures above 40° C. A further need has existed to provide a vanadium catalyst that produces more polymer i.e., has greater catalyst efficiency, under identical conditions than a conventional vanadium based catalyst such as $VCl_4$.

A further need has existed for a vanadium catalyst system that is more efficient in converting more of the vanadium into active catalyst than the heretofore described prior art $VCl_4$ catalyst. For example, with respect to tubular reactor systems such as disclosed in U.S. Pat. No. 4,540,753, use of catalyst systems containing vanadium compounds such as $VCl_4$ has shown that the requisite pre-mixing and aging of catalyst components has resulted in significant deactivation of some portion of the catalysts formed. In some cases deactivation has occurred in up to 55 mole percent of catalyst formed based on the moles of the initial vanadium compound added. Reduction in the active catalyst is characterized by consequent reduction in polymerization efficiency.

A yet further need has been the desire to find a vanadium catalyst with an expanded lifetime beyond that which is currently obtained using $VCl_4$ systems.

SUMMARY OF THE INVENTION

The novel transition metal compounds of the invention comprise either the reaction product of a trivalent transition metal compound with at least two equivalents of bidentate chelating ligands, or the reaction product of at least about two equivalents of trivalent transition metal bidentate chelates with one equivalent of a transition metal trihalide. This reaction product thus comprises a trivalent transition metal compound wherein two valencies of the trivalent transition metal are filled by bidentate chelating compounds, each of the bidentate chelating compounds having a combined hydrocarbyl constituency such that the bidentate trivalent transition metal compound is soluble in hydrocarbon solvents useful in coordination polymerization reactions. Thus the transition metal compounds of the instant invention are prepared by:

(1) reacting a transition metal trihalide, a transition metal trialkoxide or mixed tri(halide/alkoxide), or the adducts of these materials with Lewis bases, with at least about two equivalents of a bidentate chelating ligand or a mixture of different bidentate chelating ligands; or (2) reacting at least about two equivalents of a composition comprising the same or different transition metal (+3) tris chelates, alone or mixed with at least one chelating ligand, with one equivalent of a transition metal trihalide or its adduct with Lewis bases.

In the context of the invention, chelating ligands are those which contain at least two, and preferably not more than two, hetero atoms such as O, N, P or S, separated by a hydrocarbon radical providing sufficient chain length so as to allow both hetero atoms to chelate the same metal atom. The chelating ligand must have at least one easily removable positive ion which is lost on chelation to afford a uninegative, bidentate ligand.

The reactions of (1) above may be represented in chemical formulae as in A) and the reactions of (2) above may be represented as B).

$$MX_3 + 2\ LH \rightarrow XML_2 + 2HX \quad \text{A)}$$

$$MX_3 + 2\ ML_3 \rightarrow 3XML_2 \quad \text{B)}$$

where M is a transition trivalent metal, X is halogen, and L is a bidentate chelating ligand, and H is a representative positive ion (hydrogen).

Thus the bidentate transition metal compounds of this invention may be generically represented by the formula:

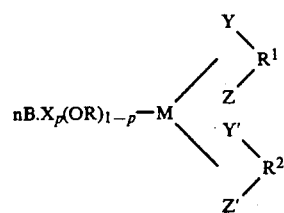
(C)

wherein B is a Lewis base adduct; n is 0–3; and M is a trivalent transition metal of Groups IB, IIIB, IV B VB, VI B, VII B and VIIIB of the Periodic Table; X is halogen., p is 0–1; R is a $C_1$ to $C_{10}$ aliphatic, alicyclic or aromatic hydrocarbon; Y and Y' and Z and Z' are heteroatoms selected from the group consisting of O, N, P and S which may be the same or different; and $R^1$ and $R^2$ are the same or different ligand groups bridging the heteroatoms and having the formula:

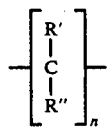

wherein n ranges from 1–5 and wherein R' and R" may be the same or different and are selected from the group consisting of hydrogen, a $C_1$ to $C_{20}$ aliphatic, alicyclic or aromatic hydrocarbon, a $C_1$ to $C_{20}$ halogenated aliphatic, alicyclic or aromatic hydrocarbon, or a ring structure wherein R' and R" connect to form a cyclic structure.

This invention also provides a novel and improved process for producing polymers by polymerization of alpha-olefins, mixtures of alpha olefins and mixtures optionally containing a diene monomer in the presence of a Ziegler-Natta type catalyst system comprising an organo aluminum compound and the bidentate trivalent transition metal compounds of invention.

DETAILED DESCRIPTION OF THE INVENTION

As indicated above in formula C), M may include transition metals of Groups IB, IIIB, IVB, VB, VIB, VIIB and VIIIB of the Periodic Table. The preferred bidentate trivalent compounds for the purposes of this invention are based on vanadium, titanium or chronium, with vanadium being most preferred. In formula C), X is selected from Cl, Br, I or F, preferably Cl.

The compounds having the structure of formula C) are prepared by reacting the specified molar quantities of metal trihalides, trialkoxides or tris chelates in an organic solvent with a member selected from the group consisting of a chelating ligand or a mixture of different chelating ligands, a transition metal tris chelate or a mixture of different transition metal tris chelates, and a mixture of a transition metal tris chelate and a chelating ligand. The chelate or chelating ligand is characterized in that it contains at least two, and preferably not more than two, hetero atoms selected from the group consisting of O, N, P and S joined by a carbon atom or a carbon chain of length to allow both hetero atoms to chelate the same metal atom. The carbon chain joining hetero atoms may generally contain from 1 to 5 carbon atoms. The chelating ligand must have at least one easily removable positive ion (such as hydrogen or metal) which is lost on chelation to afford a uninegative, bidentate ligand.

The chelate moiety of the transition metal tris chelate falls within the same scope as the structure of the chelating ligand, i.e., $M(R^1)_3$ or $M(R^2)_3$.

Categories of chelating ligands meeting the above criteria include aliphatic and aromatic mono and dibasic acids, aliphatic and aromatic diamines, diols, ketones and aldehydes, as well as heterocyclic compounds.

One category of suitable chelating ligands are aliphatic carboxylic acids or their Group IA metal salts having from 2 to 21 carbon atoms, such as represented by the structure R'-COOH wherein R is an aliphatic hydrocarbon or halogenated aliphatic hydrocarbon having 1 to 20 carbon atoms. In the context of formula C), a bidentate trivalent vanadium catalyst prepared by the reaction of $VCl_3$ and two equivalents of an R'-COOH acid would form a di-chelate, each having a single carbon atom bridging two oxygen atoms, each oxygen atom connected to the transition metal atom with R' being a pendant aliphatic group of 1-20 carbon atoms and R" being hydrogen. In the case of acetic acid, the pendant R' group would be $CH_3$. In the case of hexanoic acid, the pendant R' group would be $CH_3(CH_2)_4$-. In cases where mixed chelating ligands are employed, such as a mixture of acetic and hexanoic acids, the pendant R' group would be $CH_3$ in the $R^1$ bidentate and $CH_3(CH_2)_4$- in the $R^2$ bidentate as set forth in formula C). Preferred acids are those of the structure R'COOH wherein R' has from 2 to about 10 carbon atoms.

Another category of chelating ligand which may be employed are aromatic carboxylic acids such as benzoic acid and tertiary butyl benzoic acid and their Group IA metal salts. These ligands form bidentate ligands in the same manner as the aliphatic acids, except that R' would be a pendant aromatic group.

Aromatic and aliphatic dicarboxylic acids and carbonyl compounds (e.g., ketones and aldehydes) may also be employed as chelating ligands in accordance with the present invention, with the proviso however, that the carboxy groups be within five carbon atoms of one another. Spacing of greater than five carbon atoms will not permit the carboxy oxygens to chelate on the same vanadium atom. Suitable aliphatic dicarboxylic acids include $C_2$ to $C_5$ acids such as oxalic, malonic and glutaric acids, as well as unsaturated acids such as maleic or fumaric and their anhydrides. Suitable dibasic aromatic acids include isophthalic and terephthalic acids. Suitable ketones include 2,4-pentanedione, 1,3-butanedione, benzoyl acetone, dibenzoyl methane, dibenzoyl ethane, 3-(n-butyl)-2,4 pentanedione, and 2-hydroxyacetophenone. Another category of suitable ligands include aliphatic and aromatic diamines such as ethylene diamine or diamino benzene, and diols such as ethylene glycol and propylene glycol.

Other suitable chelating ligands include aliphatic and aromatic aldehydes having at least one hetero atom-containing substituent group such as salicaldehyde; polyhydric phenols such as resorcinol; and heterocyclic compounds with at least one hetero atom-containing substituent group such as 8-hydroxyquinoline and 2-hydroxypyridine.

In general, any bidentate, uninegative ligand fulfilling the above criteria and able to form chelate compounds with trivalent transition metals are included within the scope of this invention.

As pointed out above, the novel catalysts of this invention are prepared by:

(1) reacting transition metal trihalides or transition metal trialkoxides or the adducts of these compounds with Lewis bases such as THF, 2-methyl-tetrahydrofuran or dimethyl pyridine, with at least two equivalents of a chelating ligand in the presence of an organic solvent; or (2) reacting at least about two equivalents of a composition comprising the same or different transition metal (+3) tris chelates, alone or mixed with at least one chelating ligand, with one equivalent of a transition metal trihalide or its adduct with Lewis bases. The reaction is conducted in the presence of an organic solvent. As already indicated, the preferred transition metal is vanadium. The two vanadium (+3) tris chelates may be different, but in the preferred case are the same.

The reaction process for preparing the compounds of this invention involves heating or refluxing the aforementioned reactants in suitable solvent, preferably under inert atmosphere such as nitrogen gas, for period of time sufficient for maximum yield of the product. Reaction catalysts such as triethylamine may optionally be employed. Suitable non-coordinating hydrocarbon solvents which may be employed include aromatic and aliphatic hydrocarbons such as benzene, toluene, xylene, butane, pentane, hexane, heptane, cyclopentane, chlorobenzenes and like organic solvents, or mixtures thereof. Suitable coordinating solvents which may be used are Lewis bases such as THF, 2-methyl tetrahydrofuran, diethyl ether, dioxane, dimethylpyridine, and mixtures thereof. These coordinating solvents complex with the reactants in the formation of the chelated compounds of this invention. In general, any solvent that is characterized as a Lewis base will be operable in accordance with this invention. Mixtures of such organic solvents are also suitable for use and yield catalyst compositions varying in number and type of coordinated Lewis base molecules where both non-coordinating solvents are mixed with coordinating solvents or where different non-coordinating solvents are mixed.

The bidentate transition metal compounds of this invention are prepared by reacting one equivalent of the transition metal trihalide, trialkoxide or mixed tri (halide/alkoxide) with at least about two equivalents of the chelating ligand, or the transition metal tris chelate or the various mixtures thereof. Where mixtures of different chelating ligands, different tris chelates, or tris chelate/chelating ligand are employed, each component of such mixtures may be used in any molar ratio with respect to the other component. Molar ratios within the range of 2:1 to 1:2 respectively are preferred, and equimolar ratios are most preferred.

In the most preferred embodiment of this invention, the chelating ligands have a sufficient number of carbon atoms so that the resulting transition metal compound also will be soluble in the common organic solvents used for the solution polymerization of olefinic monomers, such solvents including aliphatic, cycloaliphatic and aromatic hydrocarbons, or halogenated versions thereof. Thus, it is preferred that the number of carbon atoms contained in the bidentate chelating moities (R1, R2 of formula C)) will equal or exceed 5 in total number.

Where the ligand is an aliphatic carboxylic acid or Group IA salt thereof, it preferably contains from three to ten carbon atoms, more preferably from five to eight carbon atoms. Hexanoic and octanoic acids and their salts are most preferred. Preferred salts are the Group I metal salts, more preferably the alkali metal salts. The preferred aromatic carboxylic acid is t-butyl-benzoic acid.

As indicated above, the novel transition metal catalysts of the present invention are useful as catalyst components in the polymerization of olefin monomers such as ethylene or propylene as well as copolymers of ethylene with at least one higher alpha-olefin. When used as such, the transition metal compounds are used in conjunction with a co-catalyst which is an organometal compound of a metal of Groups I-A, II-A, II-B or III-A of the Periodic Table. The preferred co-catalysts are organo aluminum compounds of the formula:

| $AlR_3$, | $Al(OR')R_2$, |
|---|---|
| $AlR_2Cl$, | $R_2Al$—O—$AlR_2$, and |
| $AlR'RCl$ | $AlR_2I$ |

Al$_2$R$_3$Cl$_3$,
AlRCl$_2$, where R and R' represent C$_1$ to C$_{10}$ aliphatic, alicyclic or aromatic hydrocarbon radicals which may be the same or different. The most preferred organo-aluminum compound is an aluminum alkyl sesquichloride such as Al$_2$Et$_3$Cl$_3$ or Al$_2$(iBu)$_3$Cl$_3$.

In terms of performance, a catalyst system comprised of the vanadium compounds of this invention and Al$_2$R$_3$Cl$_3$, preferably where R is ethyl, has been shown to be particularly effective. For best catalyst performance, the molar amounts of catalyst components added to the reaction mixture should provide a molar ratio of aluminum to transition metal, such as (Al/V), of at least about 2. The preferred minimum Al/V is about 4. The maximum Al/V is based primarily on the considerations of catalyst expense and the desire to minimize the amount of chain transfer that may be caused by the organo-aluminum compound (as explained in detail below). Since certain organo-aluminum compounds act as chain transfer agents, if too much is present in the reaction mixture then excessive low molecular weight products may be formed. Based on these considerations, the maximum Al/V could be about 25, however, a maximum of about 17 is more preferred. The most preferred maximum is about 15.

The catalyst system of the present invention is useful for the polymerization and copolymerization of olefin monomers to prepare polymer products such as polyethylene, polypropylene, polybutene and like materials, and are found to be particularly effective for the production of ethylene containing elastomeric copolymers. In addition, the catalytic properties can be tailored by the choice of the ligand or ligand combination surrounding the transition metal.

The ethylene-containing elastomeric polymers made in accordance with this invention are polymers that have been copolymerized with one or more higher alpha olefin monomers and optionally a diene monomer. As applied to the polymers of this invention, the terms "elastomeric" or "elastomer" are defined to mean that when they are crosslinked they are capable of recovering from large deformations quickly and forcibly. Free from diluents, the crosslinked polymers retract within one minute to less than 1.5 times their original lengths after being stretched at 18° C.-29° C. to twice their lengths and held for one minute before release.

Typically elastomers are "substantially amorphous", and when that term is used to define the ethylene-containing elastomeric polymers of this invention, it is to be taken to mean having a degree of crystallinity less than 25%, preferably less than about 15%, and more preferably less than about 10% as measured by means known in the art. The three major known methods of determining crystallinity are based on specific volume, x-ray diffraction, and infrared on measurement of heat content as a function of temperature spectroscopy. Another well-established method, based on measurement of heat content as a function of temperature through the fusion range, is now easily carried out using differential scanning calorimetric measurements. It is known that these independent techniques lead to good experimental agreement. Additionally, it is known in the art that the tendency of a particular combination of catalyst system and monomers to produce "blocky", random, or alternating polymers can be characterized by the product of the reactivity ratios defined for the given monomers under the specific reaction conditions encountered. If this product is equal to 1.0, the sequence distribution will be perfectly random; the more the product is less than 1.0, the more the monomers will approach alternating sequence; and, the more the product is greater than 1.0, the more the monomers will tend to have a "blocky" sequence distribution. Generally speaking, the segments of a polymer which crystallize are linear segments which have a number of identical (both by chemical make-up and stero-specific orientation) units in a row. A combination of such segments are said to yield "blocky" polymer. If there is little or no such sequential order within the segments making up a polymer chain, that chain will be very unlikely to conform itself into the correct shape to fit into the spatial order to a crystal and will accordingly exhibit a low degree of crystallinity. The ethylene-containing elastomeric polymers of this invention, accordingly, have a reactivity ratio product less than 2.0, preferably less than about 1.5, and more preferably less than about 1.25, and are substantially amorphous.

These ethylene-containing elastomeric polymers generally have an ethylene content that can range from about 15 to 85 wt.% of the total polymer, preferably about 30 to 85 wt. %, most preferably about 40 to 80 wt. %.

The ethylene-containing elastomeric polymer made according to this invention will also include one or more higher mono-olefins, particularly alpha-olefins having from 3 to 25 carbon atoms. The higher mono-olefins suitable for use may be branched or straight chain, cyclic and aromatic substituted or unsubstituted and are preferably alpha-olefins having from 3 to 16 carbon atoms. Illustrative non-limiting examples of preferred alph-olefins are propylene, 1-butene, 1-pentene, 1-hexene, 1-octene and 1-dodecene. Mixed olefins can also be used (e.g., propylene and 1-butene, mixed butenes, etc.). The alpha-olefin is generally incorporated into the ethylene containing elastomeric polymer in an amount of about 15 to about 85 wt. %, more preferably at about 15 to about 70 wt.% and even more preferably about 20 to about 60 wt.%.

The alpha-olefins, when substituted, should not be aromatic substituted on the 2-carbon position (e.g.. moieties such as CH$_2$=CH—Ar— should not be employed), since such an aromatic group interferes with the subsequent desired polymerization. Illustrative of such substituted alpha-olefins are compounds of the formula H$_2$C=CH—C$_n$H$_{2n}$—X' wherein n is an integer from 1 to 20 carbon atoms (preferably 1 to 10 carbon atoms), and X' comprises aryl, alkylaryl or cycloalkyl. Exemplary of such X' substituents are aryl of 6 to 10 carbon atoms (e.g., phenyl, naphthyl and the like), cycloalkyl of 3 to 12 carbon atoms (e.g., cyclopropyl, cyclobutyl, cyclohexyl, cyclooctyl, cyclodecyl, cyclododecyl and the like), alkaryl of 7 to 15 carbon atoms (e.g., tolyl, xylyl, ethylphenyl, diethylphenyl, ethylnaphthyl and the like). Also useful are alpha-olefins substituted by one or more such X' substituents wherein the substituent(s) are attached to a non-terminal carbon atom, with the proviso that the carbon atom so substituted is not in the 1- or 2-carbon position in the olefin. Included are the alkyl-substituted bicyclic and bridged alpha-olefins, of which C$_1$-C$_9$ alkyl substituted norbornenes are preferred (e.g., 5-methyl-2-norbornene, 5-ethyl-2-norbornene, 5-(2'-ethylhexyl)-2-norbornene and the like).

The ethylene-containing elastomeric polymer may also be formed of ethylene and one or more higher mono-olefins as described above, plus one or more polymerizable non-conjugated dienes. Non-conjugated dienes suitable for purposes of the present invention can be straight chain, hydrocarbon di-olefins or cycloalkenyl-substituted alkenes, having about 6 to about 15 carbon atoms, for example:

A. straight chain acyclic dienes, such as 1,4-hexadiene and 1,6-octadiene;

B. branched chain acyclic dienes, such as 5-methyl-1,4-hexadiene; 3,7-dimethyl-1,6-octadiene; 3,7-dimethyl-1,7-octadiene; and the mixed isomers of dihydro-myricene and dihydroocinene;

C. single ring alicyclic dienes, such as 1,3-cyclopentadiene; 1,4-cyclohexadiene; 1,5-cyclooctadiene and 1,5-cyclododecadiene;

D. multi-ring alicyclic fused and bridged ring dienes, such as tetrahydroindene; methyltetra-hydroindene; dicyclopentadiene; bicyclo-(2.2.1)-hepta-2,5-diene; alkenyl, alkylidene, cycloalkenyl and cycloalkylidene norbornenes, such as 5-methylene- 2-norbornene (MNB), 5-ephylidene-2- norbornene (ENB), 5-propenyl-2-norbornene, 5-isopropylidene-2-norbornene, 5-(4-cyclo pentenyl)-2-norbornene, 5- cyclohexylidene-2- norbornene and 5-vinyl-2-nor- bornene;

E. cycloalkenyl-substituted alkenes, such as allyl cyclohexene, vinyl cyclooctene, allyl cyclodecene, and vinyl cyclododecene.

Of these, the preferred dienes are dicyclopentadiene, 1,4-hexadiene, 5-methylene-2-norbornene, and 5-ethylidene-2- norbornene. Particularly preferred dienes are 5-ethylidene- 2-norbornene and 1,4-hexadiene. It will be apparent that a mix of such dienes can also be utilized. The content of the optional diene monomer in the ethylene-containing elastomeric polymer can be 0 to about 15 weight percent, and if used, preferably 0.5 to about 12 weight percent, and most preferably about 1.0 to about 6.0 weight percent.

The molecular weight range of the ethylene-containing polymers prepared by the catalyst systems of this invention as measured by NMR will typically range from about 5,000 to about 5,000,000 weight average molecular weight (Mw), more typically from about 10,000 to 500,000 Mw, most typically about 15,000 to about 350,000 Mw. Mooney viscosity ($ML_{1+8}$, 127° C.) will typically range from about 10 up to about 90, more typically about 20 to about 75.

For the polymerization reaction used in accordance with the present invention in conventional reactors, the polymerization reaction can be carried out at any temperature suitable for Ziegler catalysis such as a temperature of about $-100°$ C. to about 150° C., or preferably about 10° C. to about 100° C. and more preferably about 0° C. to about 60° C. The pressure used in the polymerization process can vary from about 0 KPa to about 3000 KPa and preferably from about 20 KPa to about 1500 KPa, most preferably about 300 KPa to about 600 KPa.

Chain transfer agents for the Ziegler-catalyzed polymerization of alpha-olefins are well known and are illustrated, by way of example, by hydrogen or diethyl zinc for the production of EPM and EPDM. Such agents are very commonly used to control the molecular weight of EPM and EPDM produced in continuous flow stirred reactors. For the essentially single active species Ziegler catalyst systems used in accordance with the present invention, addition of chain transfer agents to a continuous flow stirred tank reactor (CFSTR) reduces the polymer molecular weight but does not affect the molecular weight distribution.

Any known diluent or solvent for the reaction mixture that is effective for the purpose can be used in conducting polymerization in accordance with the present invention. For example, suitable diluents or solvents would be hydrocarbon solvents such as aliphatics, cyclo-aliphatics, and aromatic hydrocarbon solvents, or halogenated versions of such solvents. The preferred solvents are $C_{12}$ or lower straight-chain or branched-chain, saturated hydrocarbons, and $C_5$ to $C_9$ saturated alicyclic or aromatic hydrocarbons, or $C_2$ to $C_6$ halogenated hydrocarbons. Most preferred are $C_{12}$ or lower straight chain or branched-chain hydrocarbons, particularly hexane. Non-limiting illustrative examples of diluents or solvents are butane, pentane, hexane, heptane, cyclopentane, cyclohexane, cycloheptane, methyl cyclopentane, methyl cyclohexane, isooctane, benzene, toluene, xylene, chloroform, chlorobenzenes, tetrachloroethylene, dichloroethane and trichloroethane.

Additionally, it is known to incorporate "branch suppressors" when diene monomers are included in the polymerization to reduce branching. It is known in the art that certain Lewis bases, such as $NH_3$ are effective as branch suppressors. Additionally, certain alkoxy silanes, e.g , methyl silicate ($Si(OMe)_4$). ethyl silicate ($Si(OEt)_4$). etc., have been recently discovered to act as effective branch suppressors without reducing catalyst efficiency or reactivity. The particular amount of suppressor required to suppress branching will depend on the nature of the suppressor, the diolefin, the catalyst system, the Al/V ratio and the polymerization conditions. The use of excessive amounts of silicates will result in reduced catalyst activity. The silicate concentration can also be expressed in terms of Si/V mole ratio and can vary from about 0.1 to about 3.0. The vanadium and aluminum compounds can be added to the reactor either separately or premixed with one another. The silicates, optionally used as branching suppressors, should be added to the reactor separately and not in combination with any of the catalyst components in order to avoid reaction with the catalyst components and an alteration of their polymerization characteristics. Thus, the catalyst system of this invention may be used in any of the known solution polymerization processes After polymerization, the polymerization reaction mixture is quenched by known methods at the exit of the reactor. This quenching can be accomplished by the introduction into the polymerization reaction mixture (e.g., in the reactor or into polymerization product effluent stream) of water, lower alkanol, or aqueous acid (e.g. aqueous HCl) as quench liquid, generally using from 1 to 30 moles of quench liquid per mole total V and Al in the reaction mixture.

A particularly preferred process is the process described in U.S. Pat. No. 4,540,753, the disclosure of which is incorporated herein by reference. As indicated therein, the processes are carried out in a "mix-free reactor', where substantially no mixing occurs between portions of the reaction mixture that contain polymer chains initiated at different times. This typically tubular reactor polymerization provides for substantially no "back-mixing," and substantially no mixing in an axial direction.

The polymerization process described in U.S. Pat. No. 4,540,753 is conducted in such a manner and under conditions sufficient to initiate propagation of essentially all polymer chains substantially simultaneously.

This is accomplished preferably by premixing the catalyst components outside of the reactor and aging this premixed catalyst system within a range generally of from about 0.1 second up to about 200 seconds, preferably 0.5-100 seconds, most preferably 1-50 seconds. The premixing and aging are typically to be accomplished at temperatures at about 40° C. or below, preferably 25° C. or below, most preferably about 15° C.

Since chain transfer reactions during tubular reactor polymerization broaden polymer molecular weight distribution, the presence of chain transfer agents in the reaction mixture should be minimized or omitted altogether. Although difficult to generalize for all possible reactions, the amount of chain transfer agent used should be limited to those amounts that provide copolymer product in accordance with the desired limits as regards MHD and compositional dispersity. It is believed that the maximum amount of chain transfer agent present in the reaction mixture could be as high as about 0.2 mol/mol of transition metal. e.g.. vanadium, again provided that the resulting copolymer product is in accordance with the desired limits as regards MWD and compositional dispersity. Even in the absence of added chain transfer agent, chain transfer reactions can occur because propylene and the organo-aluminum cocatalyst can also act as chain transfer agents. In general, among the organo-aluminum compounds that in combination with the vanadium compound yield Just one active species, the organo-aluminum compound that gives the highest copolymer molecular weight at acceptable catalyst activity should be chosen. Furthermore, if the Al/V ratio has an effect on the molecular weight of copolymer product, that Al/V should be used which gives the highest molecular weight also at acceptable catalyst activity. Chain transfer with propylene can best be limited by avoiding excessive temperature during the polymerization as described below.

The temperature of the polymerization reaction mixture is to be controlled within the range as disclosed, to avoid overheating that could be caused by the large quantities of heat of reaction from polymerization. Feed pre-chill or appropriate heat exchange conditions are appropriate. Temperature control used to maintain the polymerization reaction temperature at any given point along the length of the tubular reactor is in accordance with the teaching of U.S. Pat. No. 4,540,753.

Good radial mixing, as opposed to axial mixing, is important and is achieved by the use of residence time/flow rate control and, optionally, radial mixing devices. Residence time can range from about 1 second up to as much as 3600 seconds, preferably 10-1800 seconds, most preferably 15-900 seconds.

As indicated above, it has been found that the novel catalyst compounds of the invention are very effective catalysts for the polymerization of ethylene/propylene elastomeric copolymers. In addition, the catalytic properties can be tailored by the choice of the ligand around the transition metal atom. These catalysts fulfill the needs of a new generation of transition metal catalysts outlined above and have an appropriate combination of desirable properties which are set forth hereinafter.

In particular, it has been found that those catalysts which have the general structure of formula C) wherein $R^1$ and $R^2$ are dissimilar ligands, have unexpected beneficial properties in the polymerization of ethylene and propylene when polymerized under parameters such as set forth in the following examples.

The unexpected properties of the novel transition metal catalyst compounds of this invention may be characterized as follows:

(i) they are soluble in hydrocarbons, most typically hexane or toluene;

(ii) they produce more polymer under identical conditions than the conventional vanadium based catalysts such as $VCl_4$. The productivity of these catalysts does not decrease as rapidly as $VCL_4$ with increases in polymerization temperature, and this improvement is available both for CFSTR process as well as for the Tubular reactor process;

(iii) compared to $VCl_4$, these catalysts are efficient in converting more of the transition metal into active catalyst, (iv) compared to $VCl_4$, these catalysts polymerize ethylene and propylene slower;

(v) compared to $VCl_4$, these catalysts tend to show decreased tendency to form blocks of ethylene and propylene in the polymer;

(vi) compared to $VCl_4$, the lifetime of the polymerization is several times larger;

(vii) compared to $VCl_4$, these catalysts are more resistant to chain transfer during the polymerization;

(viii) these catalysts will efficiently copolymerize norbornene type mono or diolefins into EPM or EPDM polymers.

It is to be understood that different embodiments of the invention may be made without departing from the spirit and scope thereof, and that the examples are illustrative rather than limiting insofar as the invention scope is concerned.

The following Examples 1-4 illustrate the preparation of vanadium catalyst compositions within the structure of formula C) above and reacted in the presence of non-coordinating solvents. Example 5 illustrates the preparation of a titanium analog.

EXAMPLE 1

25.0 g of $VCl_3$ (0.159 mol) was suspended in 350ml of dry toluene in an atmosphere of nitrogen. The toluene was heated to reflux and to this mixture was added 36.95 g (0.318 mol) of hexanoic acid dissolved in 350 ml of dry toluene. The mixture was maintained at reflux over 12 hours and during that time HCl gas was freely evolved. The HCl was absorbed in a caustic solution and titrated to indicate that a total of 0.302 moles of HCl was liberated. At the end of this period of reflux the $VCl_3$ had dissolved to yield a brown, viscous solution which was filtered free of insoluble material (0.5g), and evaporated under vacuum to yield 47.5g (94% of theory) of a brown solid, which was analyzed as V(Hexanoate)$_2$Cl.

EXAMPLE 2

50.0 g of $VCl_3$ (0.318 mol) and 63.6 g of 2,4-pentanedione (0.636 mol) were refluxed overnight in 300 ml of dry toluene. The solution changed color from green to brown at the completion of the heating period. HCl was evolved during the reaction time. The resulting brown solution was diluted with an equal volume of toluene, filtered free of insoluble material and evaporated under vacuum to yield a dark brown-green crystalline material. This was further dried under vacuum to yield 93.5 g of material, which was analyzed as V(2,4-pentanedionate)$_2$Cl (102% of theory).

EXAMPLE 3

10.0g of VCl$_3$ (0.0635) moles was suspended in 200 ml toluene and to it was added 7.37 g of hexanoic acid (0.0635 mol), 6.35 g of 2,4-pentanedione (0.0635 mol) and 12.8 gms of triethyl amine (0.127 mol). The mixture was heated for 6 hours under a nitrogen atmosphere. At the end of this period the brown liquid containing suspended material was filtered to yield a insoluble residue which as analyzed as triethyl amine hydrochloride and weighed 16.65 gms (95% of theory) when dried. The brown filtrate was dried under vacuum to yield 18.2 gms (95% of theory) of a brown solid which analyzed as V(hexanoate) (2,4-pentanedionate) Cl.

EXAMPLE 4

30.0 g of VCl$_3$ (0.1905 mole) was suspended in 500 ml dry toluene under an atmosphere of nitrogen. The mixture was heated to reflux and 33.18 g of hexanoic acid (0.2857 mole) was added. The mixture was heated to reflux for 6 hours until all evolution of HCl ceased and then purged with nitrogen to remove all traces of dissolved acid. To this material L was added 39.4 g of V(salicaldehyde)$_3$ (0.0952 mole) and the mixture was heated for 6 hours at reflux.

The resulting clear solution was diluted with 300 ml of toluene, filtered to remove undissolved solids (residue=1.3 gms) and dried under vacuum to a red brown solid which weighed 88.2 g (96% of theory), and was analyzed as V(salicaldehyde) (hexanoate)Cl.

EXAMPLE 5

25.0 g of TiCl$_3$ (0.162 mol) was suspended in 350ml of dry toluene in an atmosphere of nitrogen. The toluene was heated to reflux and to this mixture was added 37.54g (0.323 mol) of hexanoic acid dissolved in 350 ml of dry toluene. The mixture was maintained at reflux over 12 hours and during that time HCl gas was freely evolved. The HCl was absorbed in a caustic solution and titrated to indicate that a total of 0.310 moles of HCl was liberated. At the end of this period of reflux the TiCl$_3$ had dissolved to yield a brown, viscous solution which was filtered free of insoluble material (0.3g), and evaporated under vacuum to yield 49.5g (97% of theory) of a brown solid, which was analyzed as Ti(Hexanoate)$_2$Cl.

Transition metal compositions made in the presence of a coordinating solvent such as THF incorporate the solvent during the formation of the material, and may be prepared as follows:

EXAMPLE 6

36. 95 g (0.318 mol) of hexanoic acid was added to 350 ml of THF and to this mixture was added, in small portions, 12.7 g of washed sodium dispersion (Alfa-Ventron). Hydrogen was rapidly evolved and to complete the reaction the temperature of the solution was maintained at 50° C. 2 hours after the addition of sodium was complete the solution was diluted with 300 ml of fresh THF and to the mixture was added, in small aliquots. 25.0 g of VCl$_3$ (0.0159 moles). The reaction was extremely exothermic and yielded a green-brown solution. The mixture was stirred at about 50° C. overnight and the next morning it was centrifuged to remove precipitated sodium chloride. The resulting solution was dried under vacuum to yield of green-brown solid weighing 59.2 g.

EXAMPLES 7-11

A series of copolymers based on ethylene and propylene monomers were prepared in a continuous flow stirred tank reactor using the vanadium compositions of Examples 1-4 as co-catalyst components (Examples 8-11) and vanadium tetrachloride (VCl$_4$) for comparative purposes (Example 7).

Polymerization conditions were as follows:

| REACTOR CONDITIONS | |
|---|---|
| Reactor: | 1 liter continuous flow stirred tank reactor (CFSTR) |
| Temperature: | 30° C. (Condition A) |
| | 45° C. (Condition B) |
| | 60° C. (Condition C) |
| Pressure: | 500K Pa |
| Residence time: | 11 minutes |
| Agitation: | 1200 rpm |

| REACTOR FEEDS | |
|---|---|
| Ethylene: | 47.7 gm/hr |
| Propylene: | 135.2 gm/hr |
| Hexane: | 3380 gm/hr |
| Vanadium Catalyst: | 0.396 mmol/hr |
| Cocatalyst - Ethyl Aluminum Sesquichloride: | 0.975 gm/hr |

Catalyst evaluated during the polymerization in these and subsequent examples are as follows:

| CATALYST | EXAMPLE CODE | EXAMPLES |
|---|---|---|
| Tetra chloro vanadium (+4) (VCl$_4$) | 0 | 7, 12, 16, 20, 25 |
| Bis hexanoate mono chloro vanadium (+3) | 1 | 8, 13, 17, 21, 26 |
| Bis (2,4-pentanedionate) mono chloro vanadium (+3) | 2 | 9, 14, 18, 22, 27 |
| Hexanoate (2,4-Pentanedionate) mono chloro vanadium (+3) | 3 | 10, 15, 19, 23, 28 |
| Hexanoate Salicaldehyde mono chloro vanadium (+3) | 4 | 11, 24, 29 |
| Bis hexanoate mono chloro titanium | 5 | 30 |

The polymerization results as set forth in Table 1 are expressed as polymer made in the reactor in gms per hour.

TABLE 1

| | | Catalyst Productivity at Specified Temperature | | |
|---|---|---|---|---|
| Example | Catalyst Code | 30° C. | 45° C. | 60° C. |
| 7 | 0 | 85 | 53 | 39 |
| 8 | 1 | 95 | 68 | 58 |
| 9 | 2 | 92 | 64 | 51 |
| 10 | 3 | 87 | 64 | 51 |
| 11 | 4 | 90 | 73 | 56 |

It is apparent from this data that the invention catalyst systems are more efficient than VCl$_4$ in polymerizing ethylene-alpha olefin copolymers and that the increase in efficiency occurs even at a typical reactor temperature of 30° C. The comparative efficiency increases with increases in reactor temperature as shown by the data for conditions at 45° C. and 60° C.

EXAMPLES 12-15

A further series of copolymers based on ethylene and propylene monomers were prepared in a tubular reactor similar to the process described in U.S. Pat. No. 4,540,753 using the vanadium compositions of Examples 1-3 as cocatalyst components (Examples 13-15) and $VCl_4$ for comparative purposes (Example 12).

Polymerization conditions were as follows:

| REACTOR CONDITIONS | |
|---|---|
| Reactor: | ⅜ inch tubular reactor |
| Temperature: | 15° C. at the initial zone with adiabatic temperature rise along polymerization zone |
| Pressure: | 300K Pa |
| Residence Time: | 45 seconds |
| Flow Rate: | 90 liter/minute |

| REACTOR FEEDS | | |
|---|---|---|
| Monomers: | Ethylene | = 400 gms/hr |
| | Propylene | = 4000 gms/hr |
| Solvent: | Hexane | = 90.8 liter/hr |
| Catalysts: | Vanadium Catalyst | = 35.9 mmol/hr and Ethyl Aluminum Sesqui Chloride = 287.2 mmol/hr premixed for 8 sec at 10° C. for the catalyst of Example 12 and at −10° C. for all others. |

The polymerization results are shown in Table II and are expressed/as polymer made in the reactor in gms per hour.

TABLE II

| Example | Catalyst code | Polymerization Rate |
|---|---|---|
| 12 | 0 | 787 |
| 13 | 1 | 832 |
| 14 | 2 | 878 |
| 15 | 3 | 891 |

It is apparent from this data that the catalyst systems of Examples 13, 14 and 15 are significantly more effective than $VCL_4$ in polymerizing ethylene/propylene monomers in a tubular reactor process.

EXAMPLES 16-19

These examples illustrate the efficient conversion of the vanadium catalysts of this invention (Examples 17-19) to active catalyst than $VCl_4$ catalyst (Example 16).

Polymerizations were run in a tubular reactor as described under Examples 12-15. The vanadium component attains a maximum conversion to the active catalyst under certain premixing conditions determined by the concentrations of the vanadium and aluminum components and the residence time in the premixing zone and the reaction temperature. The experiment was conducted with identical concentrations of vanadium compound and the same molar ratio of aluminum to vanadium. The premixing experiment was run for the residence time of 8 seconds and the reaction temperature was varied to maximize the conversion of the vanadium component into the active catalyst.

The results shown in Table 111 are the percentage of vanadium which is converted to the active catalyst at this maximum.

TABLE III

| Example | Catalyst Code | Catalyst Conv % |
|---|---|---|
| 16 | 0 | 42 |
| 17 | 1 | 67 |
| 18 | 2 | 72 |
| 19 | 3 | 75 |

It is apparent from this data that the catalyst systems of this invention are more efficiently converted to the active catalyst than $VCl_4$.

EXAMPLES 20-24

These examples illustrate that the vanadium catalyst components of this invention (Examples 21-24) are active for a longer period of time than $VCl_4$ catalyst (Example 20).

Polymerizations were carried out in a tubular reactor experiment as set forth in Examples 12-15, but conducted isothermally at 40° C. The polymerization kinetics were analyzed as a first order decay process as indicated in Table IV below.

TABLE IV

| Example | Catalyst Code | Half-Life at 40° C. (Secs) |
|---|---|---|
| 20 | 0 | 2.5 |
| 21 | 1 | 19.8 |
| 22 | 2 | 11.6 |
| 23 | 3 | 13.8 |
| 24 | 4 | 10.0 |

It is apparent from this data that the catalysts of the invention are active for a longer period of time compared to $VCL_4$, and that the analysis indicates that compared to $VCL_4$, which has a half-life of 2.5 seconds, the catalysts of codes 1-4 live longer by several multiples of this time.

EXAMPLES 25-30

These examples illustrate the efficiency of the catalysts of this invention in the preparation of polyethylene.

In a 1.5 liter reaction vessel was introduced 800 ml of hexane. This was maintained at room temperature and ethylene was slowly bubbled in at the rate of 34 gms/hour. When the solution was saturated, 5 mmoles of Ethyl aluminum sesquichloride was added as a solution in hexane followed by a solution of 1 mmole of the transition metal catalyst compound dissolved in toluene. Polymerization of ethylene initiated rapidly to form solid insoluble polyethylene. The polymerization was maintained for 0.5 hrs with constant monomer addition. At the end of the polymerization period, the polymerization was terminated by the addition of 5 ml of isopropanol and the polymer was recovered by filtration and dried to constant weight.

The data shown in Table V are the weights of polyethylene isolated in the polymerization experiments.

TABLE V

| Example | Catalyst Code | Wt of PE (GMS) |
|---|---|---|
| 25 | 0 | 13 |
| 26 | 1 | 13.9 |
| 27 | 2 | 14.3 |
| 28 | 3 | 15.0 |
| 29 | 4 | 15.0 |
| 30 | 5 | 13.5 |

It is apparent from this data that the catalysts of codes 1-5 show superior efficiency when polymerizing ethylene compared to VCl$_4$.

EXAMPLES 31-42

Polymerization experiments were conducted in a continuous flow stirred tank reactor process wherein norbornene type monomers such as norbornene and 5-ethylidene-2-norbornene (ENB) are copolymerized employing the invention catalysts. The polymerization was conducted under the following conditions:

| REACTOR CONDITIONS: | |
|---|---|
| Reactor: | 1 liter CFSTR |
| Temperature: | 30° C. |
| Pressure: | 500K Pa |
| Agitation: | 1200 rpm |
| Residence: | 9 min |

| FEEDS: | |
|---|---|
| Hexane: | 4.11 kg/hr |
| Ethylene: | 95 g/hr |
| Propylene: | 138 g/hr |
| Vanadium catalyst: | 2.5 mmol/hr |
| Ethyl aluminum sesquichloride: | 17.5 mmol/hr |
| Norbornene monomers: | |
| Condition A: | none |
| Condition B: | Norbornene at 10.3 gms/hr |
| Condition C: | Norbornene at 20.6 gms/hr |
| Condition D: | ENB at 12.4 gms/hr + Tetraethoxysilane at .208 gms/hr |

TABLE VI

| | POLYMERIZATION RESULTS | | POLYMERIZATION RATE gms/hr | WT % MONOMER IN POLYMER |
|---|---|---|---|---|
| Example | Catalyst Code | Condition | | |
| 31 | 1 | A | 171 | 0.0 |
| 32 | 1 | B | 171 | 6.4 |
| 33 | 1 | C | 168 | 12.4 |
| 34 | 1 | D | 160 | 9.5 |
| 35 | 2 | A | 169 | 0.0 |
| 36 | 2 | B | 164 | 6.3 |
| 37 | 2 | C | 159 | 11.2 |
| 38 | 2 | D | 152 | 10.0 |
| 39 | 3 | A | 165 | 0.0 |
| 40 | 3 | B | 178 | 6.1 |
| 41 | 3 | C | 164 | 12.4 |
| 42 | 3 | D | 165 | 7.7 |

From the results shown in Table VI, it is clear that the catalyst compounds of the invention are highly effective catalysts for the copolymerization of bicyclic norbornene type monomers.

What is claimed is:

1. A catalyst composition comprising a trivalent transition metal compound wherein two valencies of the transition metal are filled by bidentate chelating compounds, each of the bidentate chelating compounds having a combined hydrocarbyl constituency such that the trivalent transition metal compound is soluble in hydrocarbon solvents.

2. The catalyst composition of claim 1 wherein said transition metal compound is a bidentate trivalent transition metal compound having the formula:

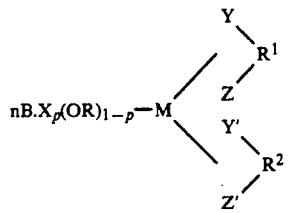

wherein B is a Lewis base adduct; n is 0-3; and M is a trivalent transition metal of Groups IB, IIIB, IV B VB, VI B, VII B and VIIIB of the Periodic Table; X is halogen; p is 0-1; R is a C$_1$ to C$_{10}$ aliphatic, alicyclic or aromatic hydrocarbon; Y and Y' and Z and Z' are heteroatoms selected from the group consisting of O, N, P and S which may be the same or different, and R$^1$ and R$^2$ are the same or different ligand groups bridging the heteroatoms and having the formula:

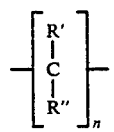

wherein n ranges from 1-5 and wherein R' and R" may be the same or different and are selected from the group consisting of hydrogen, a C$_1$ to C$_{20}$ aliphatic, alicyclic or aromatic hydrocarbon, a C$_1$ to C$_{20}$ halogenated aliphatic, alicyclic or aromatic hydrocarbon, or a ring structure wherein R' and R" connect to form a cyclic structure.

3. The compound of claim 2 wherein M is selected from the group consisting of vanadium, titanium and chromium.

4. The compound of claim 3 wherein X is chlorine and p is 1.

5. The compound of claim 3 wherein M is vanadium.

6. The compound of claim 2 wherein the ligands R$^1$ and R$^2$ are derived from an acid or mixture of acids having the structure R'COOH, or Group IA metal salts thereof, wherein R' is an aliphatic, alicyclic or aromatic hydrocarbon having from 1 to 20 carbon atoms, or a halogenated derivative thereof.

7. The compound of claim 6 wherein M is vanadium, X is chlorine, p is 1, n is 1 and Y, Z, Y' and Z' are all oxygen.

8. The compound of claim 7 wherein R' is an aliphatic hydrocarbon having from 2 to about 10 carbon atoms and R" is hydrogen.

9. The compound of claim 7 which is trivalent bis hexanoate mono chloro vanadium.

10. The compound of claim 7 which is trivalent bis titanate mono chloro vanadium.

11. The compound of claim 7 wherein R' is a substituted or unsubstituted aromatic hydrocarbon.

12. The compound of claim 11 wherein said aromatic hydrocarbon is the residium of tertiary butyl benzoic acid.

13. The compound of claim 5 wherein the ligands $R^1$ and $R^2$ are derived from aliphatic dicarboxylic acids or their Group IA salts having from 2 to 5 carbon atoms.

14. The compound of claim 5 wherein the ligands $R^1$ and $R^2$ are derived from aromatic or aliphatic ketones.

15. The compound of claim 14 wherein said ketones are selected from the group consisting of 2,4-pentanedione, 1,3-butanedione, benzoyl acetone, dibenzoyl methane, dibenzoyl ethane, 3-(n-butyl)-2,4 pentanedione and 2-hydroxyacetophenone.

16. The compound of claim 14 which is trivalent bis (2,4-pentanedionate) mono chloro vanadium.

17. The compound of claim 5 wherein the ligand $R^1$ is derived from an acid having the structure R'COOH, wherein R' is an aliphatic, alicyclic or aromatic hydrocarbon or halogenated derivative thereof having from 1 to 20 carbon atoms, and $R^2$ is derived from a different ligand.

18. The compound of claim 17 wherein $R^2$ is derived from an aromatic or alphatic ketone.

19. The compound of claim 18 which is trivalent hexanoate (2,4-pentanedionate) mono chloro vanadium.

20. The compound of claim 17 wherein $R^2$ is derived from an aromatic or aliphatic aldehyde.

21. The compound of claim 20 which is trivalent hexanoate salicaldehyde mono chloro vanadium.

22. A process for preparing a bidentate trivalent metal compound comprising reacting in the presence of an organic solvent:
(a) about one equivalent of a trivalent transition metal compound having the structure:

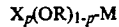
$X_p(OR)_{1-p}M$ wherein M is a trivalent transition metal of Groups IB, IIB, IVB, VB, VIB, VIIB, and VIIIB of the Periodic Table; X is halogen; p ranges from 0-1; and R is an aliphatic, aromatic or alicyclic hydrocarbon; with
(b) about two equivalents of a chelating ligand or mixture of chelating ligands having from 2 to about 21 carbon atoms and containing at least two hetero atoms selected from the group consisting of O, N, P or S joined by a carbon atom or a carbon chain of up to 5 carbon atoms.

23. The process of claim 22 wherein M is vanadium.

24. The process of claim 23 wherein p is 1 and X is chlorine.

25. The process of claim 24 wherein said organic solvent is a non-coordinating solvent.

26. The process of claim 24 wherein said organic solvent is a coordinating solvent.

27. The process of claim 24 wherein said chelating ligand comprises an acid or mixture of acids or the Group IA salts thereof having the formula R'COOH wherein R' is an aliphatic, aromatic or alicyclic hydrocarbon having from 2 to about 20 carbon atoms.

28. The process of claim 27 wherein R' is an aliphatic hydrocarbon having from 2 to about 10 carbon atoms.

29. The process of claim 28 wherein said chelating ligand comprises hexanoic acid.

30. The process of claim 24 wherein said chelating ligand comprises an aromatic or aliphatic ketone.

31. The process of claim 30 wherein said ketone is selected from the group consisting of 2,4-pentanedione, 1,3-butanedione, benzoyl acetone, dibenzoyl methane, dibenzoyl ethane, 3-(n-butyl)-2,4 pentanedione and 2-hydroxy acetophenone.

32. The process of claim 31 wherein said ketone is 2,4-pentanedione.

33. The process of claim 24 wherein said chelating ligand comprises salicaldehyde.

34. The process of claim 24 wherein said chelating ligand comprises 8-hydroxyquinoline.

35. The process of claim 24 wherein said chelating ligand comprises 2-hydroxypyridine.

36. The process of claim 27 wherein said ligand comprises a mixture of said acid and a different ligand selected from the group consisting of aromatic and aliphatic ketones or aldehydes.

37. The process of claim 36 wherein said different ligand is salicaldehyde.

38. The process of claim 36 wherein said different ligand is 2,4-pentanedione.

39. The process of claim 25 wherein said non-coordinating solvent is selected from toluene and hexane.

40. The process of claim 26 wherein said coordinating solvent is at least one Lewis base.

41. The process of claim 40 wherein said coordinating solvent comprises tetrahydrofuran.

42. A bidentate trivalent metal compound produced by the process of claim 22.

43. A bidentate trivalent vanadium compound produced by the process of claim 25.

44. A bidentate trivalent vanadium compound produced by the process of claim 26.

45. A process for preparing a bidentate trivalent metal compound comprising reacting in the presence of an organic solvent.
(a) at least two equivalents of one or more trivalent transition metal tris chelates having the structure:

$ML_3$ wherein M is a trivalent transition metal of Groups IB, IIB, IVB, VB, VIB, VIIB, and VIIIB of the Periodic Table; L is a chelating ligand having from 2 to about 21 carbon atoms and containing at least two hetero atoms selected from the group consisting of O, N, P or S joined by a carbon atom or a carbon chain of up to 5 carbon atoms; with
(b) about one equivalent of a transition metal trihalide having the structure:

$nB \cdot MX_3$ wherein B is Lewis adduct; n is 0-3, and X is halogen.

46. The process of claim 45 wherein M is vanadium.

47. The process of claim 46 wherein X is chlorine or bromine.

48. The process of claim 47 wherein said organic solvent is a non-coordinating solvent.

49. The process of claim 47 wherein said organic solvent is a coordinating solvent.

50. The process of claim 47 wherein said chelating ligand comprises an acid or mixture of acids or the Group IA salts thereof having the formula R'COOH wherein R' is an aliphatic, aromatic or alicyclic hydrocarbon having from 2 to about 20 carbon atoms.

51. The process of claim 50 wherein R' is an aliphatic hydrocarbon having from 2 to about 10 carbon atoms.

52. The process of claim 51 wherein said chelating ligand comprises hexanoic acid.

53. The process of claim 47 wherein said chelating ligand comprises an aromatic or aliphatic ketone.

54. The process of claim 53 wherein said ketone is selected from the group consisting of 2,4-pentanedione, 1,3-butanedione, benzoyl acetone, dibenzoyl methane, dibenzoyl ethane, 3-(n-butyl)-2,4 pentanedione and 2-hydroxy acetophenone.

55. The process of claim 54 wherein said ketone is 2,4-pentanedione.

56. The process of claim 47 wherein said chelating ligand comprises salicaldehyde.

57. The process of claim 47 wherein said chelating ligand comprises 8-hydroxyquinoline.

58. The process of claim 47 wherein said chelating ligand comprises 2-hydroxypyridine.

59. The process of claim 50 wherein said ligand comprises a mixture of said acid and a different ligand selected from the group consisting of aromatic and aliphatic ketones or aldehydes.

60. The process of claim 57 wherein said different ligand is salicaldehyde.

61. The process of claim 57 wherein said different ligand is 2,4-pentanedione.

62. The process of claim 48 wherein said non-coordinating solvent is selected from toluene and hexane.

63. The process of claim 49 wherein said coordinating solvent is at least one Lewis base.

64. The process of claim 53 wherein said coordinating solvent comprises tetrahydrofuran.

65. A bidentate trivalent metal compound produced by the process of claim 45.

66. A bidentate trivalent vanadium compound produced by the process of claim 48.

67. A bidentate trivalent vanadium compound produced by the process of claim 49.

* * * * *